United States Patent [19]

Ho et al.

[11] Patent Number: 5,660,181
[45] Date of Patent: Aug. 26, 1997

[54] HYBRID NEURAL NETWORK AND MULTIPLE FIBER PROBE FOR IN-DEPTH 3-D MAPPING

[75] Inventors: Zonh-Zen Ho, Hacienda Heights; Taiwei Lu, Torrance, both of Calif.

[73] Assignee: Physical Optics Corporation, Torrance, Calif.

[21] Appl. No.: 354,317

[22] Filed: Dec. 12, 1994

[51] Int. Cl.⁶ .................................................. A61B 6/02
[52] U.S. Cl. .................................................. 128/665
[58] Field of Search .................................. 128/664, 665; 356/326, 328

[56] References Cited

U.S. PATENT DOCUMENTS

| | | |
|---|---|---|
| 4,930,516 | 6/1990 | Alfano et al. . |
| 4,932,934 | 6/1990 | Dougherty et al. . |
| 5,015,463 | 5/1991 | Dougherty et al. . |
| 5,042,494 | 8/1991 | Alfano . |
| 5,059,619 | 10/1991 | Haeger et al. . |
| 5,131,398 | 7/1992 | Alfano et al. . |
| 5,142,372 | 8/1992 | Alfano et al. . |
| 5,145,863 | 9/1992 | Dougherty et al. . |
| 5,171,741 | 12/1992 | Dougherty . |
| 5,197,470 | 3/1993 | Helfer et al. ............... 128/664 |
| 5,198,460 | 3/1993 | Pandey et al. . |
| 5,217,003 | 6/1993 | Wilk .......................... 600/118 |
| 5,225,433 | 7/1993 | Dougherty et al. . |
| 5,261,410 | 11/1993 | Alfano et al. . |
| 5,293,872 | 3/1994 | Alfano et al. . |
| 5,318,023 | 6/1994 | Vari et al. . |
| 5,348,018 | 9/1994 | Alfano et al. . |
| 5,355,880 | 10/1994 | Thomas et al. ............ 128/665 |
| 5,369,496 | 11/1994 | Alfano et al. . |
| 5,379,764 | 1/1995 | Barnes et al. .............. 128/664 |
| 5,456,252 | 10/1995 | Vari et al. .................. 128/665 |

OTHER PUBLICATIONS

Laser Focus World, Marketwatch "Xillix banks on imaging technology for early cancer diagnosis", Kathy Kincade, Feb. 1994 (pp. 49 and 51).

Chemical and Laser Sciences Division, Los Alamos National Laboratory "the Optical Biopsy System", Mar. 1992, (information document 10 pages).

*Primary Examiner*—William E. Kamm
*Assistant Examiner*—George R. Evanisko
*Attorney, Agent, or Firm*—Nilles & Nilles, S.C.

[57] ABSTRACT

An apparatus for in-depth three dimensional tumor mapping including (A) a light source; (B) a multi-fiber bundle including at least one illumination fiber and at least two receiving fibers, the at least one illumination fiber being connected to the light source; (C) a spectrometer connected to the at least two receiving fibers; and (D) a hybrid neural network connected to the spectrometer, said hybrid neural network including a principle component analysis processor and a neural network classifier.

10 Claims, 4 Drawing Sheets

HYBRID NEURAL NETWORK AND MULTIPLE FIBER PROBE FOR IN-DEPTH 3-D MAPPING

BACKGROUND OF THE INVENTION

1. Field of Use

The present invention relates generally to the field of tumor mapping. More particularly, the present invention concerns tumor mapping methods, and apparatus, that use a multiple optical fiber probe. Specifically, a preferred embodiment of the present invention is directed to methods and apparatus that use a multiple fiber probe to obtain data for processing by a hybrid neural network so as to obtain an in-depth three dimensional mapping of an object, such as, for example, a tumor located within living tissue. The present invention thus relates to methods and apparatus of the type that can be termed in-depth three dimensional mapping.

2. Description of Related Art

As the technology of single photon detection has become more widely available, the technology of tumor diagnosis based on photonic detection has evolved. Heretofore, a surgeon or investigator has been able to place into a tumor region a fiber probe that is capable of both the delivery and reception of light. The distinct fluorescent emission detected at a single wavelength or an intensity spectral profile, from tumor and normal tissue has supported tumor diagnosis.

Recently, photosensitive tumor-seeking drugs with a strong absorption and large fluorescence quantum yield in the far visible or near infrared regions have become available. The characteristic spectral signature of these photosensitized drugs can improve early cancer diagnosis. Because near-infrared light can penetrate much deeper into tissue than visible and ultraviolet light, the use of such drugs makes possible tissue diagnosis at a significantly greater depth than was previously accessible.

Common endoscopic imaging has used coherent fiber bundles which is a straightforward method for direct in-vivo tissue diagnosis. The imaging system permits easy direct viewing, but such an imaging system is usable only at a macroscopic scale. Therefore, the tumor resolution with such an imaging system is relatively low. Further, imaging with such imaging systems is limited to surface sensing.

The present state of the art utilizes a single fiber probe for both laser excitation and fluorescence collection. Although this type of single fiber probe can be very sensitive for photon detection and thus indicate the presence absence of cancer, it cannot deliver such quantitative information as position, dimensions, distribution, and morphology of tumors. More importantly, because of the complicated optical properties of tissue optics, the background emission can easily mask the drug's fluorescence when a single fiber probe is being utilized.

What is therefore needed, is a highly sensitive system with a smart processing algorithm to eliminate these problems and permit accurate cancer diagnosis. No existing device can acquire quantitative tumor information through photonic spectral detection.

SUMMARY OF THE INVENTION

It is therefore an object of the present invention to provide an apparatus for in-depth three dimensional mapping comprising: (A) a light source; (B) a multi-fiber bundle including at least one illumination fiber arid at least two receiving fibers, said at least one illumination fiber being connected to said light source; (C) a spectrometer connected to said at least two receiving fibers; and (D) a hybrid neural network connected to said spectrometer, said hybrid neural network including a principle component analysis processor and a neural network classifier.

In accordance with this aspect of the present invention, a method of in-depth three dimensional tumor mapping is provided comprising (A) providing i) a light source, ii) a multi-fiber bundle including at least one illuminating fiber and at least two receiving fibers, said at least one illuminating fiber being connected to said light source, iii) a spectrometer connected to said at least two receiving fibers, iv) a hybrid neural network connected to said spectrometer, and v) a monitor displaying a representation, said monitor being connected to said hybrid neural network; (B) positioning said multi-fiber bundle proximal an object to be analyzed, said object being fluorescent; (C) illuminating said object with photons from said light source to obtain fluorescence; (D) transmitting fluorescence from said object to said spectrometer through said at least two receiving fibers; (E) transforming said fluorescence into spectra with said spectrometer; (F) transmitting spectra from said spectrometer to said hybrid neural network; (G) processing said spectra with said hybrid neural network to obtain a principal component analysis of said spectra by extracting a set of orthogonal feature vectors to represent said spectra; (H) classifying said set of orthogonal feature vectors with said hybrid neural network to obtain a set of results; and (I) transforming said representation to display said set of results.

Further in accordance with the above aspects of the present invention, an endoscope is provided where the improvement comprises (A) a multi-fiber bundle including at least one illumination fiber and at least two receiving fibers; (B) a spectrometer connected to said at least two receiving fibers; and (C) a hybrid neural network connected to said spectrometer.

Other aspects and objects of the present invention will be better appreciated and understood when considered in conjunction with the following description and drawing sheets.

| LIST OF REFERENCE NUMERALS USED HEREIN | | | |
|---|---|---|---|
| 100 | tumor | 320 | collection fibers |
| 110 | tissue | 330 | acceptance cone angle |
| 200 | excitation laser | 340 | robotic arm |
| 210 | fiber probe bundle | 350 | output fiber bundle |
| 220 | spectrometer | 360 | input quartz fiber |
| 230 | charge coupled device | 370 | sensor head |
| 240 | electronic processor | 380 | selfoc lens |
| 250 | hybrid neural network | 390 | SMA connector |
| 260 | monitor | 400 | lower power light source |
| 270 | three-dimensional map | 410 | holographic filter |
| 272 | PCA processor | 412 | Littrow grating |
| 278 | neural network classifier | 418 | detector pixel array |
| 280 | three-dimensional fiber probe | 420 | wavelength division multiplexer |
| | | 430 | two-dimensional photoarray detector |
| 290 | illumination fiber | | |
| 300 | receiving fibers | 440 | computer |
| 310 | lens | 450 | aberration compensated lens |

BRIEF DESCRIPTION OF THE DRAWINGS

The advantages and features of the present invention will become more readily apparent with reference to the detailed description which follows and to exemplary, and therefore non-limiting, embodiments illustrated in the following drawings in which like reference numerals refer to like elements and in which.

DESCRIPTION OF PREFERRED EMBODIMENTS

Figure 1A:
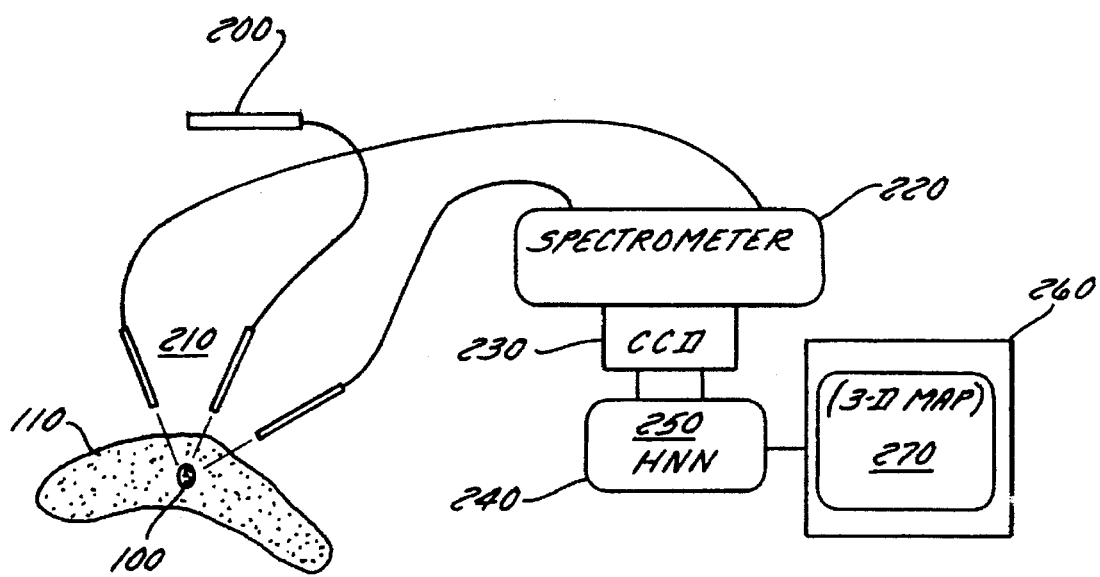
FIG. 1A illustrates a schematic view of a system for cancer detection and location according to the present invention.

The present invention and various aspects, objects, advantages, features and advantageous details thereof are explained more fully below with reference to exemplary, and therefore non-limiting, embodiments described in detail in the following disclosure and with the aid of the drawings. In each of the drawings, parts the same as, similar to, or equivalent to each over, are referenced correspondingly.

1. Resume

All the disclosed embodiments can be realized using conventional materials, components and sub-combinatorial procedures without undue experimentation. All the disclosed embodiments are useful in conjunction with systems such as are used for the purpose of detecting honors within living tissue, or for the purpose of identifying tumors within living tissue, or the like. There are virtually innumerable uses for the present invention, all of which need not be detailed here.

2. System Overview

This invention is a device that includes multiple fiber probes and a hybrid neural network (HNN) in a system for early cancer diagnosis and 3-D tissue mapping. The device is very sensitive, and thus requires minimum drug dosage and supports early, reliable and accurate cancer detection. The device is compatible with existing endoscope configurations. Therefore, the fiber probe can be inserted into the working channel of an existing endoscope with steerability for in-vivo diagnosis. The device, which preferably includes a near-infrared laser, wavelength division multiplexer, holographic elements, and filter is compact, lightweight, inexpensive, and easy to use in an operating room or office.

3. Detailed Description of Preferred Embodiments

The above-mentioned requirements are mutually contradicting and cannot be satisfied simultaneously in the case of a single fiber endoscopic probe. However, it is rendered possible to simultaneously satisfy these requirements to a certain extent by employing a probe with a multi-fiber output fiber bundle, particularly in consideration of the fact that the signals from the bundle can be processed by a hybrid neural network.

A fiber optic fluorescence system combined with a hybrid neural network is described which can be used for in-depth 3-D tumor diagnosis. Neural networks are effective for pattern recognition. The hybrid neural network (HNN) described here combines a multi-layer feed forward neural network with conventions signal processing algorithms. The advantages of the HNN for tumor diagnosis are its fast training speed, optimized architecture, and more effective recognition of small features in complex environments. The fiber optic system comprises a near-infrared laser, a beam delivery fiber, multiple fiber probes, a Raman filter and wavelength division multiplexer. By detecting pre-administered near-infrared photodynamic drugs, the system can map the 3-D fluorescence profiles of tumor tissues. The system combines distributed multiple fiber probes with a neural network to not only locate a tumor, but to show its dimensions, distribution, and morphology. The fiber probe assembly is inserted through the working channel of an endoscope; the resulting flexibility and steerability permit real-time in-depth spectroscopic mapping.

Referring to the drawings, it can be seen that this invention relaters to an endoscopic fiber probe for tumor diagnosis. In particular, the invention relates to 3-D cancer mapping.

Referring to FIG. 1A, a schematic view of a system for cancer detection and location according to the present invention is shown where tumor 100 is located within tissue 110. An excitation laser 200 is used to illuminate a region of tissue 110 near tumor 100. Fluorescence from drugs located within and around tumor 100 emit photos which are detected by fiber probe bundle 210. Fiber probe bundle 210 is connected to spectrometer 220. Spectrometer 220 is connected to charge coupled device 230. Charge coupled device 230 is electrically connected to electronic processor 240. Electronic processor 240 preferably includes hybrid neural network 250. Electronic processor 240 is connected to monitor 260. Monitor 260 preferably displays a three-dimensional map 270.

Hybrid neural network 250 can learn to identify complex patterns and waveforms by training with various examples of the objects. After a principal component analysis algorithm enhances the features of the spectrum produced by spectrometer 220, hybrid neural network 250 performs a nonlinear transformation to extract the characteristic features of the spectrum and identify the object.

Figure 1B:
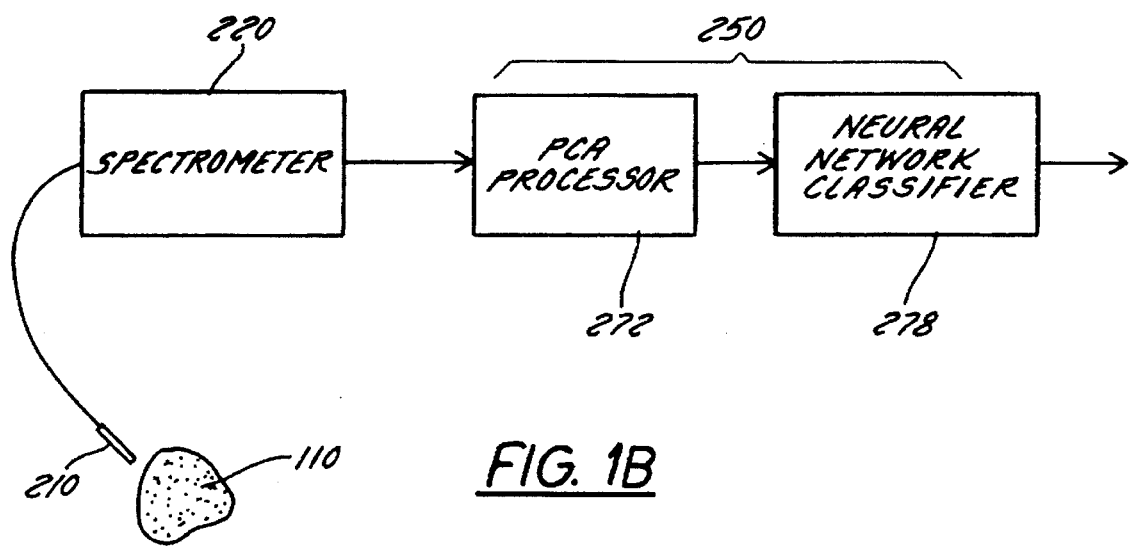
FIG. 1B illustrates a schematic view of a tumor sensing system in accordance with the present invention.

Referring now to FIG. 1B, a schematic view of a tumor sensing system in accordance with the present invention is shown. The fiber probe bundle 210, is positioned proximally tissue 110. Fiber probe bundle 210 is connected to spectrometer 220. Spectrometer 220 is connected to a principal component analysis processor 272. Principal component analysis processor 272, is connected to network classifier 278. Together, principal component analysis processor 272, and neural network classifier 278, comprise hybrid neural network 250.

Principal Component Analysis (PCA) is a vector orthogonization method that extracts key features from the signals. Assuming there are M sample spectra $V(m)$, $m=1, 2, \ldots, M$, for training the neural network, each specimen consists of N wavelength points. The task of the PCA algorithm is to extract a set of orthogonal feature vectors to represent sample spectra. The basic concept of the PCA algorithm is to project each spectra vector $M(mo)$ within the training set $\{V(m)\}$ onto an orthogonal subspace spanned by the independent vectors $V^*(m)$, $m=1, 2, \ldots, M0-1$. The first orthogonal vector $V^*(1)$ can be defined by the mean vector of the raining vectors:

$$V^*(1) = \sum_{m=1}^{M} V(m)$$

Then the procedure of generating orthogonal projection vectors can be described by the Gram-Schmidt orthogonalization algorithm:

$$V^*(mo) = V(mo) - \sum_{m=1}^{mo-1} \frac{(V(mo)V^*(m))}{\|V^*(m)\|} V^*(m)$$

where (V(m0), V*(m) denotes the vector inner product, and ‖V*(m)‖ is the norm of V*(m).

The orthogonal vector set {V*(m)} can be used as a filter set for special features extraction from the incoming spectra by the spectrometer. The projection coefficients of the orthogonal vector set can be fed into the neural network for nonlinear identification and classification.

Figure 2:
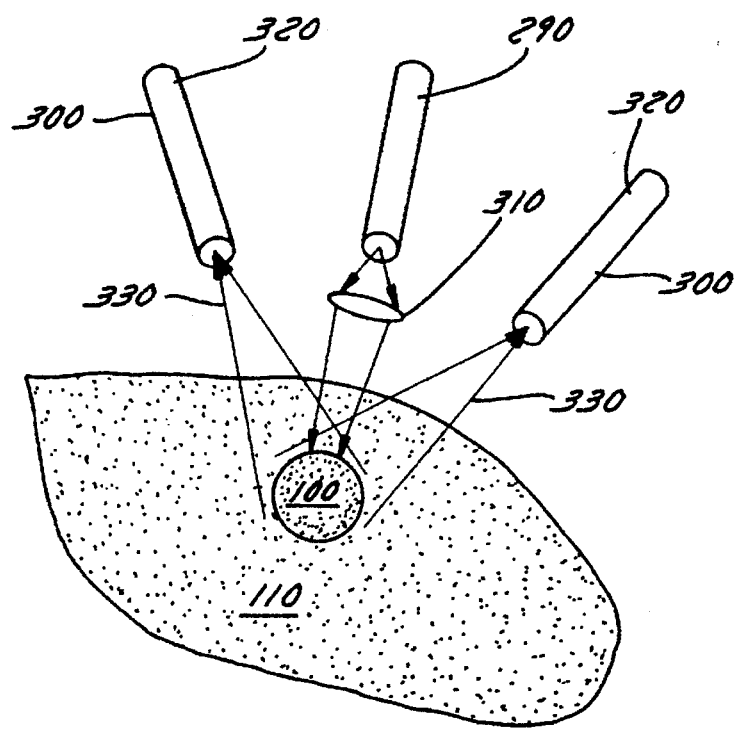
FIG. 2 illustrates a schematic view of laser light delivery and collection by a three dimensional fiber probe according to the present invention.

Referring now to FIG. 2, a schematic view of laser light delivery and collection by a three dimensional fiber probe according to the present invention is shown where three-dimensional fiber probe 280 includes three separate fibers. The three-dimensional fiber probe 280 includes an illumination fiber 290, to delivery excitation laser light to the tissue 110, under examination, and several receiving fibers 300, to collect the reflected light. A lens 310, in front of the illumination fiber 290, focuses the laser light to a certain depth in tissue 110. The receiving fibers 300 include two or more collection fibers 320, which collect the reflected light from different directions, as shown in FIG. 2. Collection fibers 320 can be located within receiving fibers 300, or be identical therewith. The minimum number of collection fibers 320 is two for a stereoscopic view of three-dimensional objects. However, an additional collection fiber, not shown in FIG. 2, can be used to confirm the location of tumor 100, thereby increasing system reliability. The output of the hybrid neural network, not shown in FIG. 2, indicates the position of tumor 100, relative to the collection fibers 320. By moving the fiber probe bundle, a doctor, or investigator, can locate and map the position and depth of the tumor 100 inside tissue 110. The resolution of the system depends on the acceptance cone angle 330 of the collection fibers 320 as well as the light scattering effect of the tissue. The narrower the acceptance cone angle 330, the higher the resolution of the system. Although the preferred embodiment shown in FIG. 2 includes the two collection fibers focused on a single location, it is within the level of ordinary skill in the art after having knowledge of the invention disclosed herein to provide additional collection fibers focused on other locations.

Figure 3:
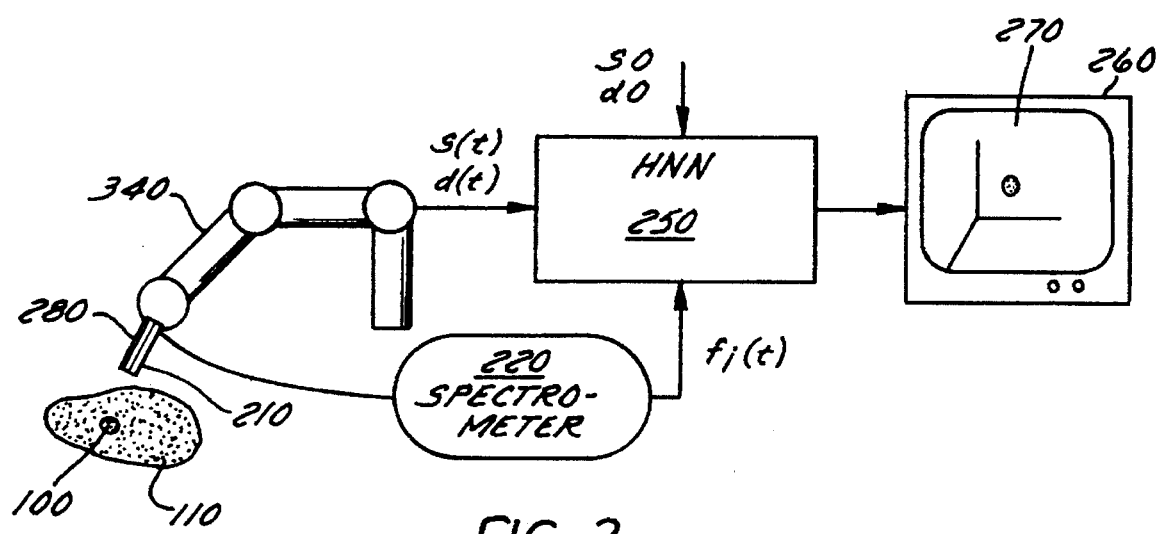
FIG. 3 illustrates a schematic view of three dimensional mapping by a tumor sensing system according to the present invention.

Referring now to FIG. 3, a schematic view of three dimensional mapping by a tumor sensing system according to the present invention is shown where S0 and d0 are the initial reference angle and distance to the surface of the tissue, s(t) and d(t) and $f_i(t)$ are the continuous angle, distance, and the fluorescent spectra, respectively; i denotes me fiber number, where the total number of sensing fibers is at least two. A robotic arm 340 positions three-dimensional fiber probe 280 which includes fiber probe bundle 210, at initial reference angle S0 and distance d0 from the surface of the tissue 110, at the beginning of an examination. Robotic arm 340 then rotates the three-dimensional fiber probe 280, while moving toward the tissue 110, surface, scanning through the three-dimensional space of the tissue 110. The fiber probe bundle 210, which can be referred to as a detector, continuously sends to hybrid neural network 250, a fluorescence spectra $f_i(t)$ and the angle and distance s(t), and d(t) of the three-dimensional fiber probe 280, where i denotes the total number of collection fibers. Although the preferred embodiment shown in FIG. 3 includes a single hybrid neural network, it is within the level of ordinary skill in the art after having knowledge of the invention disclosed herein to provide additional neural networks that are combined with additional instrumentation.

Figure 4A:
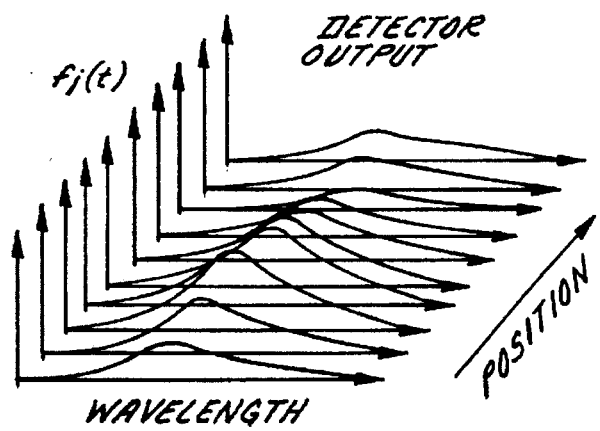
FIGS. 4A–4D illustrate schematic views of three dimensional mapping by a hybrid neural network according to the present invention.
Figure 4B:
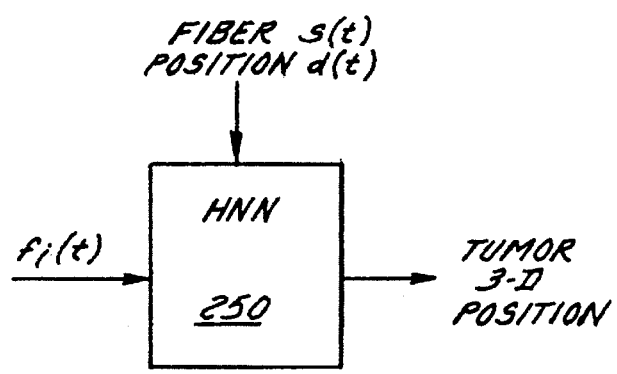
Figure 4C:
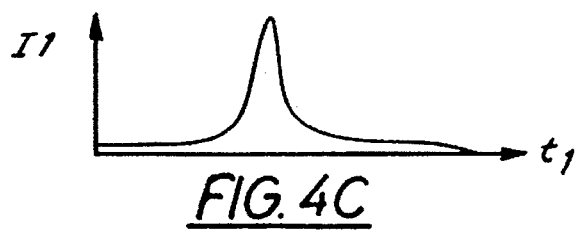
Figure 4D:
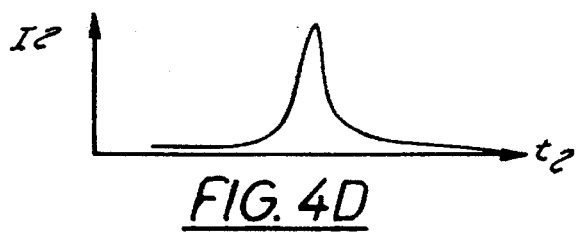

Referring now to FIGS. 4A–4D, schematic views of three dimensional mapping by a hybrid neural network according to the present invention are shown. The hybrid neural network 250 identifies the key features of the malignancy spectrum and its strength $I_i(t)$, then fuses the result with the geometric parameters defined by the location of three-dimensional fiber probe 280, not shown in FIGS. 4A–4D; to derive the three dimensional map of the tumor in the tissue, as shown in FIG. 4A. The fluorescence spectrum of the photosensitive drug, which is localized in the tumor tissue, has two to three prominent peaks between the range of 500 nm to 850 nm The output of the hybrid neural network 250, represents the probability that the spectral signal in a particular location corresponds to a tumor. Further, the hybrid neural network 250 can be trained to represent the probability that the spectral signal in a particular location corresponds to a particular type of tumor. Referring to FIG. 4A, the detector output is represented as a three-dimensional array where the fluorescence spectra $f_i$ and $_{(t)}$ is a function of both wavelength and position. Referring to FIG. 4B, the hybrid neural network 250 is shown processing fluorescence spectra $s_i(t)$ and fiber position to calculate the three-dimensional position of the tumor. Referring to FIGS. 4C–4D $t_1$ and $t_2$ denote two collection fibers and I1 and I2 represent the probabilities of the tumor location relative to each fiber, assuming that the total number of sensing fibers is two. Although the preferred embodiments shown in FIGS. 4A–4D includes the use of a three-dimensional data array, it is within the level of ordinary skill in the art after having knowledge of the invention disclosed herein to add further data dimensions for processing by the hybrid neural net.

Figure 5A:
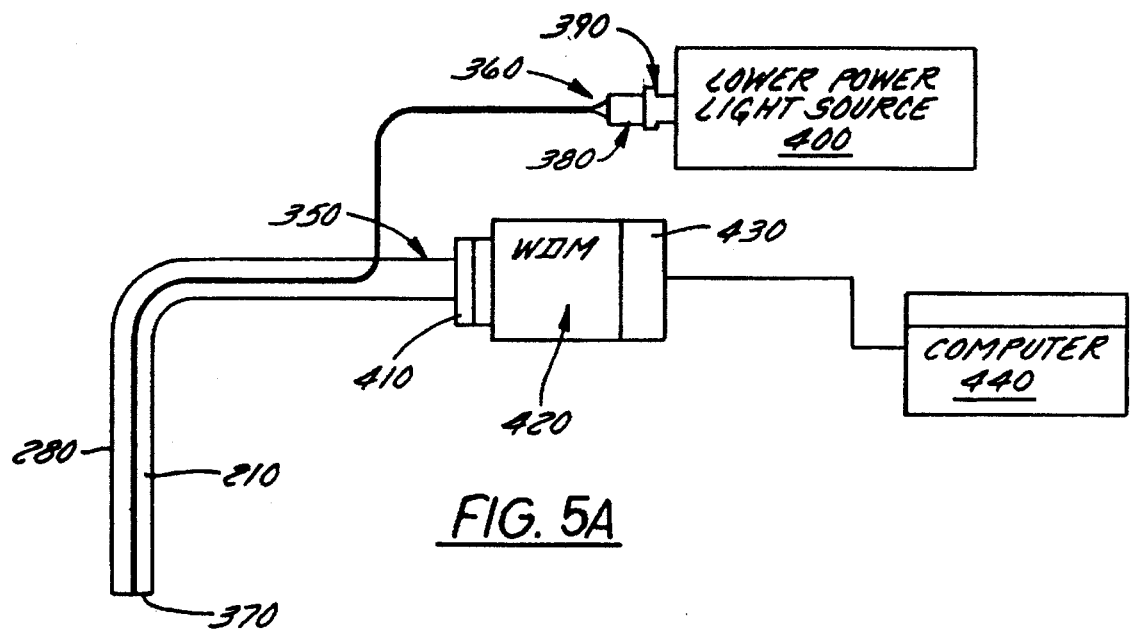
FIG. 5A illustrates a schematic view of a tumor sensing system according to the present invention.

Referring now to FIG. 5A, a schematic view of a tumor sensing system according to the present invention is shown where three-dimensional fiber probe 280, contains fiber probe bundle 210. The tumor sensing system shown in FIG. 5A comprises a photodynamic diagnosis (PDD) system.

Figure 5B:
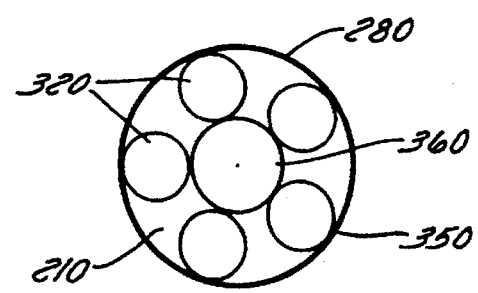
FIG. 5B illustrates a sectional view of a fiber probe bundle according to the present invention.

Referring to FIG. 5B, the three-dimensional fiber probe 280 includes an output fiber bundle 350, consisting of five collection fibers 320. The three-dimensional fiber probe 280, includes one input quartz fiber 360.

Referring again to FIG. 5A, sensor head 370 is controlled by an endoscopic manipulator, not shown in FIG. 5. Sensor head 370 is connected to selfoc lens 380, not shown in FIG. 5. Sensor head 370 is connected to selfoc lens 380, through input quartz fiber 360. Selfoc lens 380 is connected to SMA connector 390. SMA connector 390 is connected to a low power light source 400. Lower power light source 400 is preferably a laser. The sensor head 370 is connected to holographic filter 410 through output fiber bundle 350. Holographic filter 410 is connected to wavelength division multiplexer 420. Wavelength division multiplexer 420 is connected to two-dimensional photoarray detector 430. Two-dimensional photoarray detector 430 is connected to computer 440 which preferably includes a signal processor and a neural network.

In order to assure high resolution of the fluorescence spectrum, the present invention preferably uses a new optical design based on wavelength division multiplexer (WDM) techniques. Due to its very compact geometry, this WDM-based design is much more practical than conventional designs in producing spectral dispersion with very high resolution. Therefore, the use of a (WDM) containing spectrometer is preferred.

Historically, two basic spectrometer geometries were used to produce dispersion for spectroscopic applications. The first, based on the Rowland circle approach, is currently used in, e.g., the-Instrument SA spectrometer. In this case, large sizes and complex aberration corrected gratings (with respect to all primary aberrations) are necessary to provide high system resolution. The second spectrometer geometry is based on a paraxial approach, which provides the ability for reducing the size of the spectrometer and for simplifying optical component requirements. Although this approach is much more attractive for sensor applications it requires very precise wavefront optimization to preserve partial optics requirements. This includes elimination of diffraction effects on apertures, and various dimensional constraints. These aspects are often neglected in current commercial designs which lead to low sensitivity and poor resolution.

Figure 6:
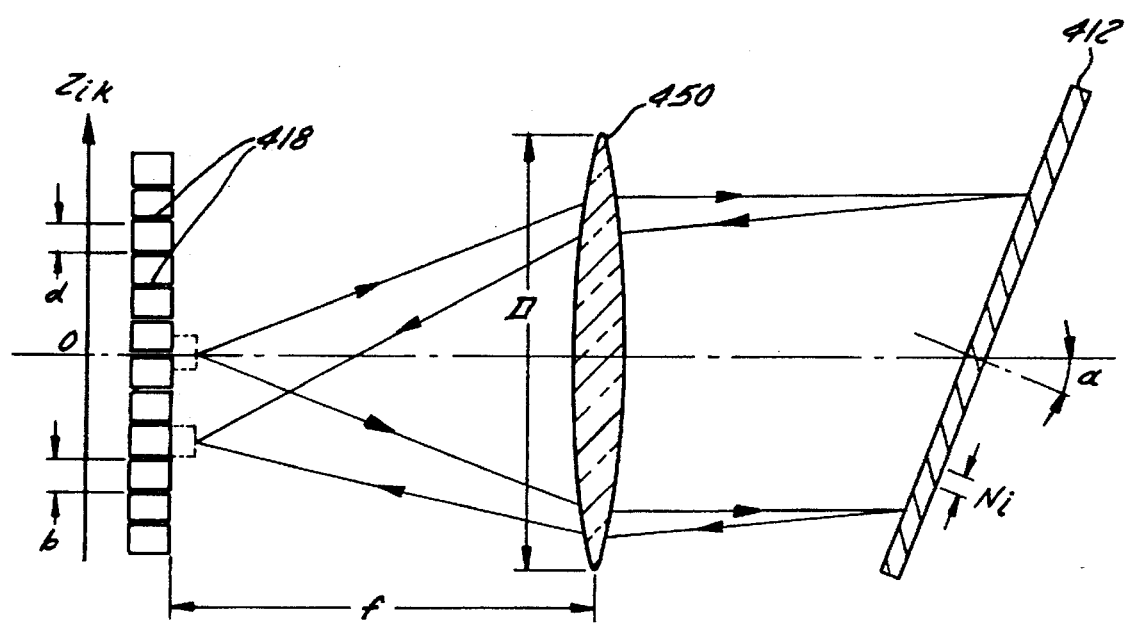
FIG. 6 illustrates a schematic view of a wavelength division multiplexing fluorescence spectrometer design in accordance with the present invention.

Referring now to FIG. 6, a paraxial geometry transmission WDM fluorescence spectrometer design is shown. Littrow Grating 412, is optically connected to detector pixel array 418, through chromatic aberration compensated lens 450.

Preferred WDM designs are based on a paraxial approach, that was developed for multichannel fiber optic communications. There are two alternative WDM designs which can be considered for fluorescence detection application.

The first alternative WDM design operates in an on-axial geometry using plane Littrow grating as a dispersive element. The second alternative WDM design utilizes a parabolic mirror and a Littrow grating. Such Littrow gratings are routinely fabricated for commercial WDMs. Without being bound by theory, it appears that the on-axial approach will lead to better resolution. Alternatively, the design with a mirror does not appear to require chromatic aberration compensation. Both designs can be evaluated using ray-tracing codes.

The photodynamic diagnosis system is designed to take advantage of modularized state of the art optical components such as, for example, laser sources, fiber bundles, holographic optical filters, wavelength division multiplexers and charge coupled device (CCD) detectors. To ensure the reliability and robustness of the photodynamic diagnosis system, all system components are integrated with solid connections through standard optical fiber connectors. The three-dimensional probe 280, which can contain multiple collection rubber bundles, has an outside diameter smaller than the working channel of the conventional endoscopes, so the three-dimensional fiber probe 280 is compatible with existing endoscope technology. The three-dimensional fiber probe 280 is feasible to construct with existing technology for one of skill in art, has a large field of view and is fully steerable.

The choice of a laser source depends primarily on the photosensitizer contained within the photodynamic drug selected for fluorescence. For example, a helium-cadmium laser (442 nm), near-infrared diode lasers (e.g., 630 or 670 nm), dye lasers, or other compact solid state lasers can be used lo excite photosensitizer photodynamic drugs containing such as, for example, photofrin, benzoporphyrin and phthalocyanine. The choice of a laser source also depends on the desired depth of tissue penetration since longer wavelength light sources provide deeper tissue penetration. Analogously, photosensitizers which emit at longer wavelengths, can permit detection at longer output fiber bundle focal lengths.

The holographic filter 410 is preferably a volume hologram that rejects background emissions and residual excitation light because the holographic filter 410 has a high optical density at wavelengths shorter than that of the photosensitizers containing drugs fluorescence. Fluorescence from the selected- photodynamic drug that are within the wavelength division multiplexer spectral range is transmitted, and background emission is removed by the holographic filter 410. Proper selection and control of the optical holographic filter 410 can greatly improve the signal to noise ratio. The three-dimensional fiber probe 280 includes both an illuminating light guide, not shown in FIG. 5, and multiple fiber bundles to collect arid carry the distributed fluorescent signal back to the spectroscopic system.

The wavelength division multiplexer 420 is set at a fixed angle to cover a 500 nm spectral range (e.g., 400–900 nm), over the size of the two dimensional photoarray detector 430. The resulting three-dimensional fluorescence profile, as shown in FIG. 4A, is used as input to the hybrid neural network 250, signal processor. The three-dimensional map 270 of the cancer, corresponding to the three-dimensional spectral image profiles, is displayed on a monitor screen for real-time diagnosis. Although the preferred embodiment shown in FIG. 5 includes an endoscopic manipulator, it is within the level of ordinary skill in the art after having knowledge of the invention disclosed herein to provide the sensor head on any type of positionable probe mount.

Conveniently, the fibers of the present invention can be made of any light transmission material. For the manufacturing operation, it is-moreover an advantage to employ a silica material.

While not being limited to any particular diagnostic identifier, preferred fluorescent drugs for use with the present invention can be identified one at a time by testing for the presence of tumor affinity. The test for tumor affinity can be carried out without undue experimentation by the use of simple and conventional in vitro bench top experiments. Among the other ways in which to seek embodiments having the attribute of physiological inertness, guidance toward the next preferred embodiment can be based on the presence of pharmacological similarities.

The foregoing descriptions of preferred embodiments are provided by way of illustration. Practice of the present invention is not limited thereto and variations therefrom will be readily apparent to those of ordinary skill in the art without deviating from the spirit and scope of the underlying inventive concept. For example photon detection could be enhanced by providing drugs whose fluorescence is a function of the type of tissue/tumor that they are located within. In addition, although fluorescent drugs are preferred for carrying out the method, any other suitable photon emitters could be used in their place. Finally the individual components need not be constructed of the disclosed materials or be formed in the disclosed shapes but could be provided in virtually any configuration which employs spatial resolution so as to provide in-depth three-dimensional mapping.

Although the best mode contemplated by the inventors of carrying out the invention is disclosed above, many additions and changes to the invention could be made without departing from the spirit and scope of the underlying inventive concept. For example, numerous changes in the details of the parts, the arrangement of the parts and the construction of the combinations will be readily apparent to one of ordinary skill in the art without departing from We spirit and scope of the underlying inventive concept.

Moreover, while there are shown and described herein certain specific combinations embodying the invention for the purpose of clarity of understanding, the specific combinations are to be considered as illustrative in character, it being understood that only preferred embodiments have been shown and described. It will be manifest to those of ordinary skill in the art that certain changes, various modifications and rearrangements of the features may be made without departing from the spirit and scope of the underlying inventive concept and that the present invention is not limited to the particular forms herein shown and described except insofar as indicated by the scope of the appended claims. Expedient embodiments of the present invention are differentiated by the appended subclaims.

The entirety of everything cited above or below is expressly incorporated herein by reference.

What is claimed is:

1. An apparatus for providing data for in-depth three dimensional mapping of an object, said apparatus comprising:
    (A) a light source;
    (B) at least one illumination fiber, said at least one illumination fiber being connected to said light source so as to illuminate said object;
    (C) at least two receiving fibers, said at least two receiving fibers being angularly displaced with respect to each other so as to receive light reflected from said object at different angles;
    (D) a spectrometer connected to said at least two receiving fibers; and
    (E) a hybrid neural network connected to said spectrometer, said hybrid neural network including a principle component analysis processor and a neural network classifier, and said hybrid neural network providing data for a three dimensional map of said object.

2. The apparatus of claim 1 further comprising a monitor for displaying said data as a three-dimensional map, said monitor being connected to said hybrid neural network.

3. The apparatus of claim 1 further comprising a robotic and which is connected to and which positions said at least one illumination fiber and said at least two receiving fibers inside a patient's body.

4. The apparatus of claim 1, further comprising a charge coupled device, said charge coupled device being connected to said spectrometer, and wherein said spectrometer further includes
    a holographic filter connected to said at least two receiving fibers, and
    a wavelength division multiplexer connected to said holographic filter.

5. The apparatus of claim 4 wherein said charge coupled device includes a two-dimensional photoarray detector and said wavelength division multiplexer includes a Littrow grating and a lens geometrically arranged for paraxial transmission.

6. The apparatus of claim 1 wherein said light source includes a selfoc lens connected to said at least one illuminating fiber, an SMA connector attached to said selfoc lens and a monochromatic light source attached to said SMA connector.

7. The apparatus of claim 1 wherein said at least one illumination fiber and said at least two receiving fibers are part of a single multi-fiber bundle.

8. In an endoscope, the improvement comprising the apparatus of claim 1.

9. A method of in-depth three dimensional tumor mapping comprising:
    (A) producing an initial representation;
    (B) providing
        i) a light source,
        ii) a multi-fiber bundle including at least one illuminating fiber and at least two receiving fibers, said at least one illuminating fiber being connected to said light source,
        iii) a spectrometer connected to said at least two receiving fibers,
        iv) a hybrid neural network connected to said spectrometer and
        v) a monitor displaying said initial representation, said monitor being connected to said hybrid neural network;
    (C) positioning said multi-fiber bundle proximal an object to be analyzed, said object being fluorescent;
    (D) illuminating said object with photons from said light source to obtain fluorescence;
    (E) transmitting fluorescence from said object to said spectrometer through said at least two receiving fibers;
    (F) transforming said fluorescence into spectra with said spectrometer;
    (G) transmitting spectra from said spectrometer to said hybrid neural network;
    (H) processing said spectra with said hybrid neural network to obtain a principal component analysis of said spectra by extracting a set of orthogonal feature vectors to represent said spectra;
    (I) classifying said set of orthogonal feature vectors with said hybrid neural network to obtain a set of results; and
    (J) transforming said initial representation to display said set of results with said monitor.

10. The method claim 9 wherein extracting said set of orthogonal feature vectors includes generating said set of orthogonal feature vectors with a Gram-Schmidt orthogonalization algorithm.

* * * * *

UNITED STATES PATENT AND TRADEMARK OFFICE
CERTIFICATE OF CORRECTION

PATENT NO. : 5,660,181
DATED : August 26, 1997
INVENTOR : Zonh-Zen Ho

It is certified that error appears in the above-identified patent and that said Letters Patent is hereby corrected as shown below:

Col. 1, line 52, delete "rumors," and insert --tumors,--.

Col. 1, line 66, delete "arid" and insert --and--.

Col. 2, line 4, delete "principle" and insert --principal--.

Col. 3, line 36, delete "honors" and insert --tumors--.

Col. 4, line 1, delete "conventions" and insert --conventional--.

Col. 4, line 27, delete "photos" and insert --photons--.

Col. 4, line 67, delete "raining" and insert --training--.

Col. 5, line 13, delete "(V(mO)" and insert --(V(mo)--.

Col. 5, line 57, delete "me" and insert --the--.

Col. 6, line 19, after "850 nm insert --. --.

Col. 7, line 6, after "the" delete "-".

Col. 8, line 29, after "is" delete "-".

Col. 8, line 63, after "from" delete "We" and insert --the--.

Col. 9, line 30, delete "principle" and insert --principal".

Col. 9, line 38, delete "and" and insert --arm--.

Claim 3, line 37, delete "and" and insert --arm--.

In the drawings, sheet 2, the reference numeral 280 with an arrow should be applied to the three-dimensional fiber probe assembly and should point generally at the illumination fiber 290 and the receiving fiber 300.

UNITED STATES PATENT AND TRADEMARK OFFICE
CERTIFICATE OF CORRECTION

PATENT NO. : 5,660,181
DATED : August 26, 1997
INVENTOR(S) : Zonh-Zen Ho

It is certified that error appears in the above-identified patent and that said Letters Patent is hereby corrected as shown below:

In the drawings, sheet 2, the reference numeral 280 with an arrow should be applied to the three-dimensional fiber probe assembly and should point generally at the illumination fiber 290 and the receiving fiber 300.

Signed and Sealed this

Twentieth Day of June, 2000

*Attest:*

Q. TODD DICKINSON

*Attesting Officer*  *Director of Patents and Trademarks*